United States Patent [19]

Martinez

[11] 4,127,133
[45] Nov. 28, 1978

[54] BONDED CONTROLLED RELEASE NEEDLE-SUTURE COMBINATIONS

[75] Inventor: Miguel Martinez, Baltimore, Md.

[73] Assignee: Ethicon, Inc., Somerville, N.J.

[21] Appl. No.: 857,648

[22] Filed: Dec. 5, 1977

Related U.S. Application Data

[63] Continuation-in-part of Ser. No. 700,374, Jun. 28, 1976, abandoned.

[51] Int. Cl.$^2$ ............................................. A61B 17/06
[52] U.S. Cl. ....................................... 128/339; 163/1
[58] Field of Search ................ 128/335.5, 339; 163/1, 163/5; 223/102

[56] References Cited

U.S. PATENT DOCUMENTS

| | | | |
|---|---|---|---|
| 2,928,395 | 3/1960 | Forbes et al. | 128/335.5 |
| 3,394,704 | 7/1968 | Dery | 128/339 |
| 3,799,169 | 3/1974 | Beroff et al. | 128/339 |
| 3,963,031 | 6/1976 | Hunter | 128/339 |

*Primary Examiner*—Dalton L. Truluck
*Attorney, Agent, or Firm*—Wayne R. Eberhardt

[57] ABSTRACT

Needle-suture combinations are provided wherein a needle having an axial opening in the blunt end thereof for receiving a suture is bonded to the suture with a hot melt wax composition having sufficient bonding strength to secure the needle to the suture during surgical procedures, but which allows the needle to be deliberately removed from the suture by a sharp tug at the completion of the surgical procedure. Needle pulloff values in the range of 1 to 56 ounces (0.028 to 1.58 kg) are readily obtained.

20 Claims, 3 Drawing Figures

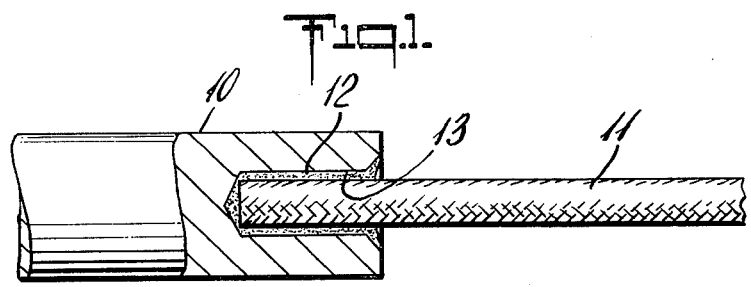
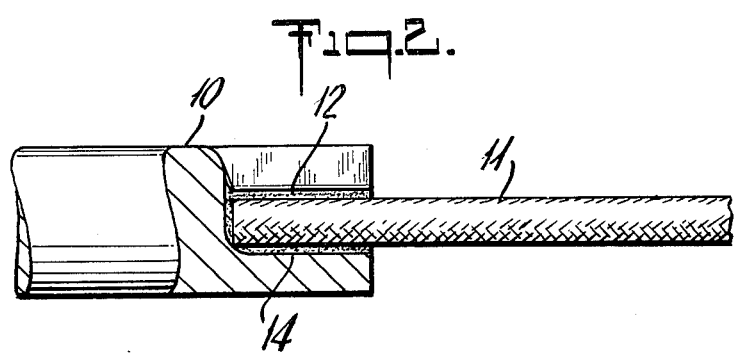

BONDED CONTROLLED RELEASE NEEDLE-SUTURE COMBINATIONS

CROSS-REFERENCE TO RELATED APPLICATIONS

This application is a continuation-in-part of my co-pending application, Ser. No. 700,374, filed June 28, 1976 now abandoned.

BACKGROUND OF THE INVENTION

This invention relates to needle-suture combinations and more particularly to needle-suture combinations wherein the needle is attached to the suture in a nonpermanent manner which allows the needle to be deliberately pulled off the suture after completion of the suturing procedure.

In many surgical procedures, surgeons use an interrupted suturing technique which employs a suture thread and an eyed needle. The needle is threaded by the nurse and the surgeon takes one pass through the tissue using a needle holder. He slips the needle off the suture, returns the needle to the nurse, and is ready for another threaded needle from the nurse. An assistant follows behind and ties each suture.

Some surgeons find this technique preferable to using a needled suture which requires cutting the needle from the suture with a scissors after each pass. However, the time required for threading individual needles delays the suturing procedure which is undesirable for the welfare of the patient and efficient utilization of expensive operating room time.

It has recently been suggested to use needle-suture combinations in which the needle and the suture are readily separable from each other after completion of the suturing procedure to provide the surgeon with the convenience of needled sutures without the inconvenience of requiring the needle to be cut off each suture. Several methods have been devised for preparing needle-suture combinations in which the pulloff values, or the force required to separate the needle from the suture by a straight, steady pull is within the desired range. One approach to this problem is described in U.S. Pat. No. 3,890,975 where the needle is attached to the suture by controlled swaging so that the force required to pull the needle off the suture is from about 3 to 26 ounces (0.085-0.736 kg). The needles are attached with sufficient security to perform regular suturing procedures, and yet are readily removed by the deliberate action of the surgeon upon completion of the procedure.

Another approach to controlled release needle-suture combinations is described in U.S. Pat. No. 3,779,169 where a suture is bonded in an open channel of a surgical needle with an adhesive composition which allows the suture to be peeled from the channel by a force of about 3 to 26 ounces when the suture is at an angle of 90° to the needle channel. Other issued U.S. patents describing needle-suture combinations having controlled release properties include U.S. Pat. Nos. 3,875,946; 3,924,630; 3,926,194; 3,949,756; and 3,943,933.

Many of the prior art controlled release needle-suture combinations depend upon swaging to attach the needle to the suture. Controlled needle release values in the desired range are obtained either by controlling the degree of swaging, by partially withdrawing the suture from the swaged needle until the holding forces are reduced to the desired pulloff values, or by providing the securely swaged suture with a breakable segment adjacent the needle. Variations in suture composition or size, or in the size and finish of the needle barrel opening can affect needle attachment and make it difficult for the suture manufacturer to maintain pulloff values within the desired range.

U.S. Pat. No. 3,779,169 supra depends upon adhesive forces rather than compression by mechanical swaging to obtain the desired release values, but is only effective with open channel needles which allow the suture to be peeled out of the channel.

Controlled release needle-suture combinations of the prior art have generally been characterized by a needle pulloff value within the range of 3 to 26 ounces. While this range is considered to be the preferred range for such needle-suture combinations, the *U.S. Pharmacopeia* has adopted a needle pulloff range of 0.028 to 1.59 kg (1 to 56 ounces) for sutures with "removable needles" and size 5-0 and larger as the standard for the suture industry.

It is accordingly an object of the present invention to provide a needle-suture combination having a removable needle within the specifications of the *U.S. Pharmacopeia*, i.e., with a needle pulloff value within the range of 1 to 56 ounces. It is a further object of the present invention to provide a needle-suture combination having a needle pulloff value within the preferred range of 3 to 26 ounces. It is a yet further object of the present invention to provide a controlled release needle-suture combination wherein the suture is secured within the axial opening of a surgical needle by means of a bonding composition which provides the needle with a pulloff value within the range of from about 1 to 56 ounces.

While adhesively bonded needle-suture combinations using drilled needles are known as described, for example, U.S. Pat. Nos. 2,928,395 and 3,394,704, conventional adhesives suggested in these references such as the polyepoxides, polyamides, polyesters, and urea resins do not reliably and consistently give needle pulloff values within the desired range for controlled release applications. These references are rather directed toward providing permanently attached needles having certain minimum, but no maximum, limits on needle attachment. The security of attachment of eyeless needles to absorbable surgical sutures or to nonabsorbable surgical sutures is prescribed in the *U.S. Pharmacopeia*, Vol. XVIII at page 944 (also see *U.S. Pharmacopeia*, Vol. XVII, p. 919). It has been the practice of suture manufacturers in the U.S. and abroad to securely attach the suture to the needle by swaging or with an adhesive so that the minimum pullout values recited in the *U.S. Pharmacopeia* are met or exceeded.

SUMMARY

In accordance with the present invention, there is provided a needle-suture combination comprising a needle having a pointed end and a blunt end with an axial opening in the blunt end, and a suture, one end of which is received in the axial opening of the needle and held therein by a bonding agent comprising a wax composition. The bonding agent may be any animal, vegetable, mineral or synthetic wax which has a melting point above about 45° C. and which provides a needle pulloff value within the range of 1 to 56 ounces at room temperature. Needles are conveniently attached to the sutures by a method wherein the needle opening is charged with molten wax, the tip of the suture is inserted into the needle opening, and the needle cooled to solidify the wax surrounding the suture tip.

BRIEF DESCRIPTION OF DRAWINGS

FIG. 1 is an enlarged elevation, partially in cross section, of the blunt end of a drilled surgical needle having a surgical thread secured therein by a wax bonding agent.

FIG. 2 is an enlarged elevation, partially in cross section, of the blunt end of a preclosed channel surgical needle having a surgical thread secured therein by a wax bonding agent.

FIG 3 is a view of a bonded needle-suture combination in accordance with the present invention.

DESCRIPTION OF PREFERRED EMBODIMENTS

The needle-suture combinations of the present invention comprise the elements of a surgical needle, a surgical suture, and a wax composition bonding agent.

The needles useful in the practice of the present invention are conventional surgical needles having a pointed end and a blunt end, and having an axial opening in the blunt end for receiving the suture. The needle may be fabricated of carbon steel or stainless steel. The pointed end may be a smooth tapered point or a shaped point with one or more cutting edges. The opening in the blunt end may be a drilled hole or a preclosed channel.

The suture may be any conventional multifilament surgical thread material such as braided silk, polyester or nylon, or twisted cotton or linen. Alternatively, the suture may be a monofilament material such as catgut or collagen. Synthetic monofilament sutures having very low surface friction characteristics such as conventional polyethylene or polypropylene may also be used, but care must be taken to assure needle pulloff values to not fall below acceptable minimums. Since the release of needles from such sutures usually occurs by a separation between the suture and the bonding agent, improved bonding and higher needle pulloff values are obtained by simply roughening the tip of the suture prior to needle attachment to improve the security of the bond. Multifilament sutures which tend to fray when cut may be resin or wax coated to unify the tip for easier insertion into the needle, as described in U.S. Pat. No. 3,890,975.

The bonding agent may be any wax composition having a melting point above about 45° C. and which has a sufficient degree of bonding strength to provide a needle pullout value within the desired range of from about 1 to 56 ounces and preferably from about 3 to 26 ounces.

As used herein, the term "wax compositions" includes waxes and waxlike materials which, although not technically true waxes, nevertheless possess many of the attributes of waxes and are generally recognized to be useful as wax substitutes. "It would seem highly desirable to include in our broad definition of wax all of the waxlike substances irrespective of source, since in the art of production or reproduction, we aim to have before us the whole field of waxes or waxlike substances from which we can select those which best suit our needs. Waxes are used in the arts because of their peculiar physical characteristics— seldom because of their chemical nature. " (*The Chemistry and Technology of Waxes* by Albin H. Worth, 2nd Ed., 1956; p. 3).

The term "wax" is defined according to *Hackh's Chemical Dictionary*, 4th Ed., to mean "a substance having the properties: (a) crystalline to microcrystalline structure; (b) capacity to acquire gloss when rubbed (distinction from greases); (c) capacity to produce pastes or gels with suitable solvents or when mixed with other waxes; (d) low viscosity at just above the melting point (distinction from resins and plastics); (e) low solubility in solvents for fats at room temperature. " Waxes derived from animal, vegetable and mineral sources are included along with synthetic waxes which are primarily esters of high molecular weight fatty acids and high molecular weight alcohols.

In general, waxes may be classified as natural wax, fossil or earth wax, petroleum wax, or synthetic wax. Natural waxes include waxes from insects (beeswax), animals (woolwax) and plants (palm tree, candelilla, cotton and hemp wax). Fossil and earth waxes include montan wax and certain paraffin waxes. Petroleum waxes include rod wax, paraffin wax, and microcrystalline wax. Synthetic waxes include polyethylene wax, ethylene copolymer wax, carbowax and halogenated hydrocarbon waxes. All these and many other waxes which have application in the present invention are described in *The Chemistry and Technology of Waxes, supra*. However, not all waxes are useful in the present invention. Only those waxes or wax formulations which have a melting point above about 45°C. and which have sufficient bonding power to secure the needle to the suture with a pulloff value of from about 1 to 56 ounces are suitable for the practice of the present invention. Preferably, the melting point of the wax is between about 65° C. and 200° C. for ease and security of attachment. Wax melting point is determined by the "Standard Open End Capillary Tube" method of the American Wax Importers and Refiners Association, Inc., as described in *Wax Sampling and Test Methods*, Nov. 1960.

One particularly preferred wax is candelilla. Candelilla is a wax extracted from the coating of a shrub that grows in the arid regions of Mexico and the American Southwest. Candelilla is a relatively hard, brittle wax, having a Shore Durometer hardness value of 99–100 at 25° C. Official specifications for pure refined candelilla wax as published by the Americal Wax Importers and Refiners Association include: melting point 68.5° to 72.5° C., flash point 241° C., paraffinic hydrocarbons 45 percent minimum.

Candelilla and other waxes useful in the present invention may be formulated with each other or with nonwax polymers, resins, rubbers, pigments, extenders and the like in order to control the melting point, hardness, color, viscosity or bonding strength of the wax. For example, waxes such as candelilla and/or paraffin may be formulated with ELVAX, a wax-compatible ethylene/vinyl acetate copolymer (a product of E. I. duPont de Nemours & Company). ELVAX is reported to be a general-purpose resin designed for use with paraffin and microcrystalline waxes to provide good toughness and flexibility at moderate melt viscosity. Blending of ELVAX with petroleum waxes effectively improves the bonding strength of that wax. (DuPont Bulletin PL 14-171 "ELVAX Vinyl Resins").

The waxes and wax compositions of the present invention are distinguished from resins and plastic adhesives by having a low viscosity just above the melting point. A viscosity of less than about 20 centipoise at a temperature 10° C. above the melting point of the composition is particularly preferred, although higher viscosity compositions can be used. Low melt viscosities permit the suture to be readily inserted into the wax-charged hole of the needle, and allow the wax to flow uniformly around the suture as required to obtain uniform an consistent needle pulloff values.

The present invention, is illustrated by the following examples where a variety of wax compositions are used to secure needles to sutures of differing sizes and materials. In the preparation of these examples, conventional drilled needles were used. The opening in the needle was substantially filled with the selected wax. When ready for suture attachment, the needle barrel was heated to melt the wax, and the suture was inserted the full depth of the hole, allowing any excess wax to exude from the needle opening. The needle barrel was then chilled to a temperature below the melting point of the wax to solidify the wax and secure the suture. Needle pulloff values were determined at room temperature (about 22° C.).

| | | Examples | | |
|---|---|---|---|---|
| No. | Wax | Suture size-material | Needle Bore Dia. × Depth Millimeters | Pulloff ozs. |
| 1 | Pure Candelilla | 2-0 Gut | 0.48 × 1.84 | 15.7 ± 3.2 |
| 2 | " | 0 VICRYL* | 0.55 × 1.27 | 12.3 ± 2.2 |
| 3 | " | 0 Silk | 0.55 × 1.84 | 14.0 ± 4.5 |
| 4 | Formulation A | 2-0 Cotton | 0.48 × 1.84 | 10.2 ± 3.1 |
| 5 | " | 0 Gut | 0.55 × 1.84 | 24.5 ± 3.8 |
| 6 | " | 4-0 Gut | 0.33 × 1.59 | 12.1 ± 1.1 |
| 7 | " | 1 Gut | 0.63 × 1.97 | 25.2 ± 3.3 |
| 8 | " | 0 Nylon | 0.55 × 1.84 | 22.5 ± 2.9 |
| 9 | Formulation B | 1 Gut | 0.63 × 1.97 | 16.4 ± 4.1 |
| 10 | Formulation C | 3-0 Silk | 0.40 × 1.71 | 14.6 ± 1.9 |
| 11 | " | 0 Silk | 0.55 × 1.84 | 20.8 ± 1.9 |
| 12 | Formulation D | 0 Silk | 0.55 × 1.84 | 20.3 ± 4.3 |
| 13 | " | 0 VICRYL* | 0.55 × 1.84 | 17.4 ± 3.8 |
| 14 | " | 2-0 VICRYL* | 0.48 × 1.84 | 16.6 ± 4.4 |
| 15 | " | 2-0 Silk | 0.48 × 1.84 | 16.0 ± 3.0 |
| 16 | Formulation E | 0 Silk | 0.55 × 1.84 | 11.0 ± 2.3 |
| 17 | Paraffin (m.p. 150° F.) | 0 Silk | 0.55 × 1.84 | 3.1 ± 1.5 |
| 18 | " | 2-0 Silk | 0.48 × 1.84 | 3.4 ± 1.8 |
| 19 | " | 2-0 Silk (siliconized) | 0.48 × 1.84 | 0.84 ± 0.85 |

Formulation
A - Sealing wax described in U.S. 3,843,312
B - 10/40/50 Candelilla/ELVAX 310/Paraffin
C - 65/35 Candelilla/ELVAX 310
D - 95/5 Candelilla/ELVAX 310
E - 50/50 Candelilla/Beeswax
*Trademark of Johnson & Johnson or Subsidiary.

EXAMPLE 20

Size 0 VICRYL* suture was attached to a needle having a bore diameter x depth of 0.55 × 1.84 mm using a 90/10 mixture of candelilla/ELVAX 310. For seven samples tested, the average pulloff value was 35 ounces with a range of pulloff values from 34 to 37 ounces.
*Trademark of Johnson & Johnson or Subsidiary.

EXAMPLE 21

Size 1 black braided silk was attached to a needle having a bore diameter x depth of 0.63 × 1.97 mm using the sealing wax of U.S. Pat. No. 3,843,312. For 21 samples tested, the average pulloff value was 39 ounces with a range of pulloff values from 33 to 58 ounces. This example illustrates the preparation of a needle-suture combination having a removable needle in the upper range of the limits for needle pulloff values adopted by the *U.S. Pharmacopeia.*

In the preceding examples, all VICRYL, silk and nylon sutures were braided multifilament sutures. Cotton was a twisted multifilament suture. All multifilament sutures, except silk No. 18 and 19, were resin tipped prior to needle attachment to unify the strand.

As illustrated by the above examples, a variety of suture materials may be attached to surgical needles with different wax compositions and formulations to obtain desired needle pulloff values. The selection of wax for any particular needle-suture combination is quickly and easily made on an experimental basis to obtain the desired needle pulloff characteristics.

In general, for any given needle-suture combination, needle pulloff values will increase as wax hardness is increased. For example, candelilla wax is a hard, brittle wax which will provide higher needle pulloff values than paraffin wax. This is illustrated by a comparison of Examples 3 and 17 in the preceding table. Using candelilla wax as a standard, needle pulloff values may be increased or decreased by formulating candelilla with other materials as illustrated, for example, in Examples 11, 12 and 16 of the preceding table.

The surface characteristics of the suture also play a part in determining needle pulloff values. Smooth monofilament sutures such as polypropylene, for example, typically have significantly lower pullout values than comparably sized multifilament sutures. Surface coatings on multifilament sutures which tend to reduce surface irregularities and friction may also reduce suture pullout value compared to uncoated sutures as illustrated, for example, in Examples 18 and 19 comparing plain and siliconized silk.

Preferred needles for use in the present invention are drilled needles having a bore diameter of 1.05 to about 2.0 times the diameter of the suture. The needle bore should be as small as possible while permitting convenient insertion of the suture. Since it is desirable for surgical reasons to keep needle diameters small so that the puncture wound is small and filled by the suture, needle bore diameters in excess of 2.0 times the suture diameter are not recommended even though needle pulloff values in the desired range can be obtained with such larger bores.

With specific reference to the drawings,

FIG. 1 illustrates needle 10 having drilled and chamfered hole 13. Suture 11 is bonded in hole 13 by wax composition 12 which substantially fills hole 13.

FIG. 2 illustrates needle 10 having axial opening 14 formed by a preclosed channel. Suture 11 is bonded in opening 14 by wax composition 12.

FIG. 3 illustrates a needle-suture combination of the present invention wherein suture 11 is bonded to needle 10 by means of a wax composition which provides a needle pulloff value of from about 1 56 ounces.

The inventive concept of the present invention resides in the use of waxes or waxlike compositions for needle attachment to surgical sutures. Heretofore, waxes have been used as a suture coating to improve the lubricity thereof, and waxes have been suggested for use in combination with swaging to reduce the suture pullout value in order to obtain controlled release properties. Waxes, however, unlike adhesives, have not heretofore been suggested for use as the sole means of needle attachment. The discovery that wax compositions not only provide a means for quickly and easily attaching needles to sutures, but that needles so attached have pulloff values within a narrow range desired for controlled release needle-suture combinations, and further that the variability of pulloff values for needles so attached is exceptionally low represents a substantial advance in the art of constructing controlled release needle-suture combinations. Wax attachment is unique in providing a means for assembling controlled release needle-suture combinations in a variety of suture sizes, compositions and structures with a single attachment method and a simple technique.

In assembling the needle-suture combination of the present invention, the opening in the needle is preferably charged with the wax composition prior to insertion of the suture. The amount of wax charged to the needle opening is preferably just sufficient to fill the opening when the suture tip is inserted therein. If greater amounts of wax are used, the excess will simply exude from the needle opening when the suture is inserted, and be lost. If lesser amounts of wax are used, needle pulloff values will be correspondingly lower and variability of pulloff values may increase. As an alternative to charging the needle opening with the wax, the tip of the suture may be dipped in the wax prior to insertion into a preheated needle. Such a method, however, is not preferred since the entrapment of bubbles in the needle opening or incomplete bonding about the suture tip may result in variations in needle pulloff values.

Many variations of the present invention beyond those specifically disclosed herein will be apparent to those skilled in the art and it is understood that such variations are included within the scope of the present invention. In particular, there are an infinite number of wax compositions and formulations which are useful in the practice of the present invention, and the present invention is accordingly not limited to any particular composition. There are also a number of steps which may be taken with regard to needle bore or suture-tip configurations in order to modify needle pulloff values. For example, the needle bore may be roughened, threaded, or otherwise modified to improve wax adhesion. Conversely, the needle bore may be polished to reduce wax adhesion. Likewise, the surface of the tip of the suture to be attached to the needle may be polished or roughened to decrease or increase wax adhesion. Yet other variations and embodiments of the present invention will be apparent to those skilled in the art in the invention is accordingly not limited except as set forth in the following claims.

What is claimed is:

1. In an unswaged needle-suture combination comprising a needle having a sharp end and a blunt end and having an axial opening in said blunt end, and a suture, one end of which is secured in said axial opening of said needle solely by means of a bonding agent, the improvement comprising utilizing as the bonding agent a wax composition having a melting point above about 45° C. and having a bonding affinity for the needle-suture combination which provides a needle pulloff value of from about 1 to 56 ounces at room temperature.

2. A needle-suture combination of claim 1, wherein the diameter of the axial opening is 1.05 to 2.0 times the diameter of the suture secured in said hole.

3. A needle-suture combination of claim 1, wherein the axial opening in the needle is a drilled hole.

4. A needle-suture combination of claim 1, wherein the axial opening in the needle is a closed channel.

5. A needle-suture combination of claim 1, wherein the needle pulloff value is from about 3 to 26 ounces.

6. A needle-suture combination of claim 1, wherein the wax composition has a melting point of from about 65° C. to about 200° C.

7. A needle-suture combination of claim 1, wherein the wax combination comprises a wax having a crystalline to microcrystalline structure.

8. A needle-structure combination of claim 1, wherein the wax composition has a viscosity of less than about 20 centipoise at a temperature 10° C. above the melting point.

9. A needle-suture combination of claim 1, wherein the wax composition comprises a wax selected from the group consisting of natural wax, fossil wax, earth wax, petroleum wax, and synthetic wax.

10. A needle-suture combination of claim 1, wherein the wax composition is comprised of candelilla wax.

11. A needle-suture combination of claim 1, wherein the wax composition is comprised of a paraffin or microcrystalline wax and an ethylene/vinyl acetate copolymer.

12. A needle-suture combination of claim 11, wherein the wax is candelilla.

13. A needle-suture combination of claim 11, wherein the wax is paraffin.

14. A needle-suture combination of claim 11, wherein the wax is a mixture of paraffin and candelilla.

15. A method of preparing a needle-suture combination wherein the needle has a pulloff value of from about 1 to 56 ounces at room temperature which comprises:
 (1) providing a needle having a sharp end and a blunt end and having an axial opening in the blunt end;
 (2) charging the opening in said needle with a wax composition having a melting point above about 45° C.;
 (3) inserting the end of a suture into the opening of the needle while the wax composition contained in said opening is in a molten state; and
 (4) cooling the needle to solidify the wax composition in the opening while maintaining the end of the suture in said opening,
whereby said suture is bonded to said needle in said needle opening by said solid wax composition.

16. A method of claim 15, wherein the axial opening in said needle is a drilled hole.

17. A method of claim 15, wherein the axial opening in said needle is a closed channel.

18. A method of claim 15, wherein said wax composition is maintained at a temperature of from the melting point of said composition to about 200° C.

19. A method of claim 15, wherein the needle is allowed to cool after insertion of the suture by exposure to ambient air.

20. A method of claim 15, wherein the needle pulloff value is from about 3 to 26 ounces.

* * * * *